US007655185B2

(12) United States Patent
Watanabe

(10) Patent No.: US 7,655,185 B2
(45) Date of Patent: Feb. 2, 2010

(54) POLYMER SAMPLE ANALYZER

(75) Inventor: Chuichi Watanabe, Koriyama (JP)

(73) Assignee: Frontier Laboratories Ltd., Fukushima (JP)

( * ) Notice: Subject to any disclaimer, the term of this patent is extended or adjusted under 35 U.S.C. 154(b) by 625 days.

(21) Appl. No.: 11/298,504

(22) Filed: Dec. 12, 2005

(65) Prior Publication Data

US 2007/0009385 A1    Jan. 11, 2007

(30) Foreign Application Priority Data

Jul. 5, 2005    (JP)    ............................. 2005-196597

(51) Int. Cl.
- G01N 33/00 (2006.01)
- G01N 21/00 (2006.01)
- G01N 17/00 (2006.01)
- G01N 33/44 (2006.01)
- G01N 30/02 (2006.01)

(52) U.S. Cl. .................... 422/68.1; 422/53; 422/83; 422/89; 436/85; 73/865.6

(58) Field of Classification Search ........................ None
See application file for complete search history.

(56) References Cited

U.S. PATENT DOCUMENTS 5,646,358 A * 7/1997 Tikhtman et al. .......... 73/865.6
2005/0120811 A1   6/2005 Hardcastle, III

FOREIGN PATENT DOCUMENTS

JP    2000-035422 A    2/2000
NL    8 900 432 A    9/1990

OTHER PUBLICATIONS

Wolfram Schnabel, "Principles and Practical Applications", Shokabo, Tokyo, 1993, pp. 120-121 Translated by Junkichi Sohma.

(Continued)

*Primary Examiner*—Jill Warden
*Assistant Examiner*—Neil Turk
(74) *Attorney, Agent, or Firm*—Arent Fox LLP

(57) ABSTRACT

Provided is a polymer sample analyzer from which chemical findings on the optical deterioration of a polymer material are available in a very short time. The analyzer is equipped with a gas phase component production unit for producing a plurality of gas phase components, a carrier gas introduction unit for introducing a carrier gas into the gas phase component production unit, a separation unit for separating the gas phase components into each component, and a detection unit 5 for detecting the each component thus separated. The analyzer is equipped further with a UV irradiation unit for exposing the polymer sample to UV ray, an atmospheric gas introduction unit for introducing an atmospheric gas into the gas phase component production unit and a gas switching unit for switching a gas to be introduced into the separation unit between the carrier gas and the atmospheric gas. Under the atmosphere of a gas introduced from the atmospheric gas introduction unit, the polymer sample is deteriorated and decomposed by exposure to UV ray from the UV irradiation unit. After deterioration and decomposition, a gas to be introduced into the separation unit 4 is switched to the carrier gas by the gas switching unit and the gas phase components are introduced into the separation unit by the aid of the carrier gas.

4 Claims, 5 Drawing Sheets

OTHER PUBLICATIONS

Fumio Ide, "Practical Polymer Materials Classified by Their Properties", Kogyo Chosakai Publishing Inc., 2002 pp. 232-233 and 253.

N. Grassie, "Developments in Polymer Degradation—7", Chemistry Department, Elsevier Applied Science Publishers, 1987, pp. 194-197.

Norman Grassie, et al., "Polymer Degradation and Stabilisation", New York, NY, USA, Cambridge University Press, 1985, pp. 68-69, 78-79.

* cited by examiner

POLYMER SAMPLE ANALYZER

BACKGROUND OF THE INVENTION

1. Field of the Invention

The present invention relates to a polymer sample analyzer for analyzing polymer materials such as plastics.

2. Description of the Related Art

In our modern society, polymer materials such as natural rubbers and plastics, as well as metal materials such as steel, play an important role. The polymer materials are now indispensable for our daily life as materials for various films, fibers, containers and the like.

It is known that when the polymer materials are used for a long period of time, their physical or chemical properties deteriorate gradually owing to external factors. The deterioration is mainly caused by heat, light, mechanical stress or the like and it also occurs by the biological or chemical reaction. Of these, the deterioration caused by light is presumed to occur because optical energy cleaves their polymer structure and radicals formed thereby cause an oxidation chain reaction ("Polymer Degradation—Principles and Practical Applications—", written by Wolfram Schnabel, translated by Junkichi Sohma, published by Shokabo, 1993; "Practical Polymer Materials Classified by Their Properties", Kogyo Chosakai Publishing Inc., 2002; "Developments in Polymer Degradation—7", N. Grassie, Elsevier Applied Science, 1987).

Tests on optical deterioration have conventionally been conducted by exposing a polymer material to real sunlight outdoors or exposing it to the light from an arc lamp, which is close to sunlight, by using a weathermeter. When the weathermeter is used, humidification is sometimes conducted simultaneously with the exposure to the light from an arc lamp.

The above-described tests are however accompanied with the following inconveniences. It takes from several months to several years to get results of the exposure test of a polymer material outdoors, while the test using a weathermeter requires large facilities and a lot of money and moreover, it takes from several weeks to several months to get its test results. The results of the above-described tests relate to the deterioration on the surface of the sample to be observed visually or under a microscope, or to mechanical properties such as tensile strength after deterioration so that it is impossible to obtain a chemical finding on the progress mechanism of deterioration of the polymer itself constituting the polymer material or various additives such as antioxidant and UV absorber contained in the polymer material.

SUMMARY OF THE INVENTION

An object of the present invention is to overcome the above-described inconveniences and provide a polymer sample analyzer by which chemical findings on the optical deterioration of a polymer sample are available in a very short time.

In order to attain such an object, the present invention provides a polymer sample analyzer, comprising a gas phase component production unit for producing a plurality of gas phase components, a carrier gas introduction unit for introducing a carrier gas into the gas phase component production unit, a separation unit for separating the gas phase components introduced therein via a sample introduction portion into each of the component, and a detection unit for detecting the components separated by the separation unit, wherein the gas phase component production unit comprises, inside thereof, a UV irradiation unit for irradiating the polymer sample with UV ray, an atmospheric gas introduction unit for introducing a predetermined atmospheric gas into the gas phase component production unit, and a gas switching unit for switching a gas to be introduced into the separation unit between the carrier gas and the atmospheric gas, and the polymer material is, under the atmosphere of the predetermined atmospheric gas introduced from the atmospheric gas introduction unit, exposed to UV ray from the UV irradiation unit to cause its deterioration and decomposition, thereby forming a plurality of gas phase components and, after the deterioration and decomposition of the polymer sample, the gas introduced into the separation unit is switched from the atmospheric gas to the carrier gas by the gas switching unit to introduce the gas phase components into the separation unit by the aid of the carrier gas.

In the polymer sample analyzer of the present invention, a polymer sample made of a polymer material such as plastic is introduced into the gas phase component production unit and then, exposed to UV ray from the UV irradiation unit under the atmosphere of a predetermined gas introduced from the atmospheric gas introduction unit. By this operation, the polymer sample is deteriorated and decomposed by the UV ray and a plurality of gas phase components can be produced.

The exposure to the UV ray may be carried out at room temperature. It is however preferred to equip the gas phase component production unit with a heating unit and carry out the exposure while heating the polymer sample by the heating unit. Heating of the polymer sample by the heating unit makes the surface of the polymer material sensitive and promotes its deterioration and decomposition.

As the gas to be introduced from the atmospheric gas introduction unit, helium, nitrogen, oxygen, air and the like can be used for example. The gas may be humidified. When the gas to be introduced from the atmospheric gas introduction unit is humidified air, a plurality of gas components containing the component produced by the action of ozone produced by exposing the air to UV ray or water in the air on the deterioration product obtained by exposure to UV ray are available.

In the polymer sample analyzer of the present invention, when the deterioration and decomposition of the polymer sample are completed, the gas to be introduced into the separation unit is switched from the atmospheric gas to the carrier gas by the gas switching unit. This switching of the gas to be introduced into the separation unit from the atmospheric gas to the carrier gas may be attained either by switching all the gases in the polymer sample analyzer to the carrier gas or by switching the gas only in the separation unit to the carrier gas. The gas phase components are then introduced into the separation unit by the aid of this carrier gas. The separation unit is equipped with, for example, a separation column such as capillary column and the plurality of gas phase components are separated into each component by this separation unit.

The each component thus separated by the separation unit is detected by the detection unit. As the detection unit, a mass spectrometer can be used for example.

As a result, the polymer sample analyzer of the present invention makes it possible to present chemical findings within a very short period of time from several minutes to several hours that what components are generated by the optical deterioration of the polymer constituting the polymer material or of the various additives contained in the polymer material such as antioxidant and UV absorber. In addition, the polymer sample analyzer of the present invention permits presumption of the progress mechanism of the deterioration or the like based on the above-described finding.

The polymer sample analyzer of the present invention is preferably equipped further with a flow rate control unit for controlling the flow rate of the gas phase components to be introduced into the separation unit by discharging a portion of the gas phase components from the sample introduction portion. The polymer sample analyzer of the present invention can introduce a proper amount of the gas phase components into the separation unit depending on the sensitivity necessary for analysis by controlling the flow rate of the gas phase components with the flow rate control unit.

The polymer sample analyzer of the present invention is preferably equipped further with a gas phase component concentrator for concentrating the gas phase components on the side of the sample introduction portion of the separation unit, and a gas phase component cooling unit for cooling the gas phase components at the gas phase component concentrator. According to the gas phase component cooling unit, when a plurality of gas phase components produced by the gas phase component production unit are introduced into the separation unit via the sample introduction portion, these gas phase components can be cooled by the sample introduction portion side of the separation means, trapped by the gas phase concentrator and concentrated. It is therefore possible to prevent the elution of a low boiling point compound contained in the gas phase components from the separation unit and detect the low boiling point compound reliably by the detection unit.

DESCRIPTION OF THE PREFERRED EMBODIMENTS

Referring to accompanying drawings, an embodiment of the present invention will next be described more specifically.

Figure 1:
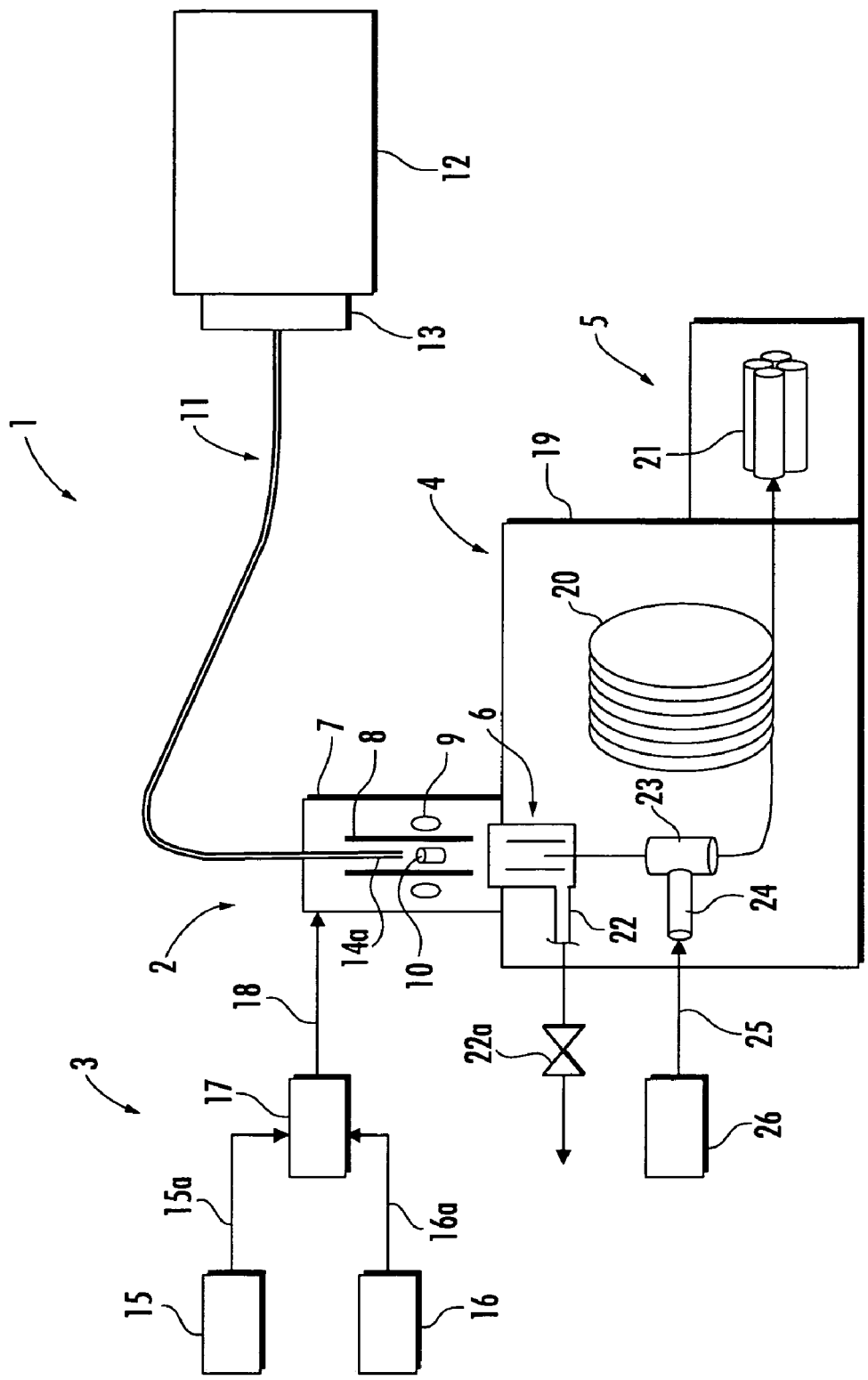
FIG. 1 is a schematic cross-sectional view illustrating a structure example of the polymer sample analyzer according to the present invention.

As illustrated in FIG. 1, a polymer sample analyzer 1 according to this embodiment is equipped with a gas phase component production unit 2 for producing a plurality of gas phase components from a sample made of a polymer material such as plastic (which sample will hereinafter simply be called "polymer sample"); a gas introduction unit 3 for introducing a carrier gas or a predetermined atmospheric gas into the gas phase component production unit 2; a separation unit 4 for separating the plurality of gas phase components introduced therein into each component; and a detection unit 5 for detecting the component separated by the separation unit 4. The gas introduction unit 3 is connected to the separation unit 4 via a sample introducing portion 6.

The gas phase component production unit 2 is equipped with a silica tube 8 disposed in a housing 7 and a heater 9 disposed on the outer circumferential side of the silica tube 8. The silica tube 8 has an upper portion through which a sample vessel 10 can be inserted and a lower portion connected to the sample introducing portion 6. As such a gas phase component production unit 2, a vertical microfurnace pyrolyzer ("PY-2020iD", trade name) which is a product of Frontier Lab, Ltd. can be used, for example.

The gas phase component production unit 2 according to this embodiment is further equipped with a UV irradiation unit 11. The UV irradiation unit 11 is equipped with a light source 12 such as a deuterium lamp, an optical filter 13 for selectively transmitting ultraviolet light having a wavelength of 400 nm or less from lights irradiated from the light source 12, and an optical fiber 14 connected to the optical filter 13. In the UV irradiation unit 11, a tip portion 14a of the optical fiber 14 is inserted from the upper end portion of the silica tube 8 in order to irradiate UV ray to the polymer sample in the sample vessel 10. The optical fiber 14 is protected by a resin coating layer (not illustrated) disposed on the outer circumferential surface thereof. This resin coating layer is however peeled at the end portion 14a which is to be inserted into the silica tube 8 and the end portion has, instead of the resin coating layer, a coating layer (not illustrated) made of a glass member such as glass tube made of silica glass or the like.

The gas introduction unit 3 is equipped with a carrier gas source 15 of a gas such as helium and an atmospheric gas source 16 of a gas such as helium, nitrogen, oxygen, air or humidified air. The carrier gas source 15 and atmospheric gas source 16 are connected to a gas switching device 17 via a carrier gas pipe 15a and an atmospheric gas pipe 16b, respectively. The gas switching device 17 is connected to the gas phase component production unit 2 via a gas pipe 18. The gas pipe 18 is opened above the silica tube 8 in the housing 7.

The separation unit 4 is equipped with a temperature controllable oven 19 and a separation column 20 such as capillary column disposed in the oven 19. The detection unit 5 is equipped with a detector 21 such as quadrupole mass spectrometer. As an apparatus having both the separation unit 4 and detection unit 5, a GC/MS system ("Model 5972GC/MS system", trade name), which is a product of Hewlett Packard, can be used.

The sample introduction portion 6 has an upper portion thereof connected to the lower portion of the silica tube 8 and a lower portion thereof connected to the separation column 20, while it has a split vent tube 22 between the upper and lower end portions thereof. The split vent tube 22 serves as a flow rate controlling unit for opening a switching valve 22a to release the air, thereby discharging a portion of the gas phase components introduced from the silica tube 8; and introducing a proper amount of the above-described gas phase components into the separation column 20 depending on the sensitivity necessary for analysis.

A gas phase component concentrator 23 is disposed on the outer circumferential side of the sample introduction portion 6 of the separation column 20 and the separation column 20 is inserted through the gas phase component concentrator 23. To the gas phase component concentrator 23, a refrigerant injection nozzle 24 for injecting a refrigerant, for example, liquid nitrogen is attached in a direction perpendicular to the separation column 20 inserted. The refrigerant injection nozzle 24 is connected to a liquid nitrogen source 26 via a liquid nitrogen pipe 25.

The refrigerant injection nozzle 24 serves as a gas phase component cooling unit for injecting liquid nitrogen to a portion of the separation column 20 inserted into the gas phase component concentrator 23, thereby cooling, at this portion, the gas phase components introduced into the separation column 20. The gas phase components are cooled by the refrigerant injection nozzle 24 at the portion of the separation column 20 inserted into the gas phase component concentrator 23, whereby they are trapped at this portion and concentrated. As an apparatus equipped with the gas phase component concentrator 23 and refrigerant injection nozzle 24, a cooling and trapping apparatus ("MicroJet Cryo-Trap"), which is a product of Frontier Lab, Ltd. can be used, for example.

The polymer sample analyzer 1 as illustrated in FIG. 1 has only one atmospheric gas source 15, but a plurality of atmospheric gas sources 15 for atmospheric gases such as helium, nitrogen, oxygen and air may be disposed respectively. In this case, the gas switching device 17 switches between a carrier gas and the plurality of atmospheric gases or switches between one atmospheric gas and another atmospheric gas.

Operation of the polymer sample analyzer 1 of this Embodiment using polystyrene as the polymer sample will next be described.

The polymer sample is prepared, for example, by forming a thin film having a thickness of 0.1 mm or less from 60 μg of polystyrene on the bottom of the sample vessel 10 in the cup form. As the sample vessel 10, a vessel made of a stainless steel already subjected to inactivation treatment can be used.

In the polymer sample analyzer 1, a gas is switched to a gas to be introduced into the gas phase component production unit 2 by the gas switching device 17 and then, an atmospheric gas such as humidified air is introduced from the atmospheric gas source 16 into the gas phase component production unit 2 via the atmospheric gas pipe 16a and gas pipe 18. Under the humidified air atmosphere, the sample vessel 10 having the thin polystyrene film formed on the bottom thereof is inserted from the upper end portion of the silica tube 8 disposed in the gas phase component production unit 2 into a predetermined position inside thereof.

The tip portion 14a of the optical fiber 14 is then inserted from the upper end portion of the silica tube 8 into the inside thereof and the polystyrene inside of the sample vessel 10 is heated by the heater 9 while exposed to UV ray. The heater 9 raises the temperature gradually from room temperature and heats the polystyrene at a temperature of about 100° C.

When the polystyrene is exposed to UV ray, it produces a plurality of gas phase components owing to deterioration and degradation. The above-described heating by the heater 9 increases the active energy on the surface of the polystyrene thereby enabling to promote deterioration.

The gas phase components are then introduced into the separation column 20 via the sample introduction portion 6. At this time, in the polymer sample analyzer 1, the switching valve 22a of the split vent tube 22 is opened. By the opening of the switching valve 22a, the split vent tube 22 is opened to the air and at the same time, the separation column 20 having a small inner diameter becomes fluid resistance, whereby the flow rate of the gas phase components introduced into the separation column 20 can be controlled and their amounts can be adjusted properly depending on the sensitivity necessary for analysis. Control of the flow rate by the split vent tube 22 is however not necessary when the amount of the gas phase components produced by the gas phase component production unit 2 is, without control, suited for the sensitivity necessary for analysis.

In the polymer sample analyzer 1, when the gas phase components are introduced into the separation column 20, the gas phase components are cooled in a portion of the separation column 20 inserted into the gas phase component concentrator 23 by liquid nitrogen injected from the refrigerant injection nozzle 24 and are trapped by the portion. As a result, the gas phase components are collected and concentrated in the portion of the separation column 20 inserted into the gas phase component concentrator 23.

In the polymer sample analyzer 1, the gas phase components are trapped in the portion of the separation column 20 inserted into the gas phase component concentrator 23 so that elution of a low boiling point compound contained in the gas phase components from the separation column 5 can be prevented. In addition, when the polymer sample such as polystyrene is heated at a temperature of about 100° C. by the heater 9, it is possible to collect all the deterioration and decomposition products in the portion of the separation column 20 inserted into the gas phase component concentrator 23, which leads to improvement in the separation accuracy by the separation column 20.

In the polymer sample analyzer 1, trapping of the gas phase components by the injection of liquid nitrogen from the refrigerant injection nozzle 24 is not required when the deterioration and decomposition product generated by the gas phase component production unit 2 is a high boiling point compound.

Then, the gas to be introduced into the gas phase component production unit 2 is switched by the gas switching device 17, whereby helium is introduced as a carrier gas from the carrier gas source 15 into the gas phase component production unit 2 via the carrier gas pipe 16a and gas pipe 18. The humidified air fed from the atmospheric gas source 16 may cause deterioration of the separation column 20 if it enters into the separation column 20 so that the humidified air must be replaced by helium sufficiently.

When the humidified air is replaced by helium sufficiently, exposure to UV ray and injection of liquid nitrogen from the refrigerant injection nozzle 24 are stopped and the temperature of the oven 19 is raised. As a result, desorption of the gas phase components concentrated in the portion of the separation column 20 inserted into the gas phase component concentrator 23 occurs and they are separated into each component by the separation column 20. Then, the each component is detected by the detection unit 5. The detection results by the detection unit 5 are output as chromatogram or mass spectrum.

In the gas phase component production means 2, the polystyrene is then deteriorated and decomposed by exposing it to UV ray at 100° C. for a predetermined time under the atmosphere of humidified air. The chromatogram when the exposure time to UV ray is 15 minutes is shown in FIG. 2, that when the exposure time to UV ray is 30 minutes is shown in FIG. 3, and that when the exposure time to UV ray is 18 hours is shown in FIG. 4.

Figure 2:
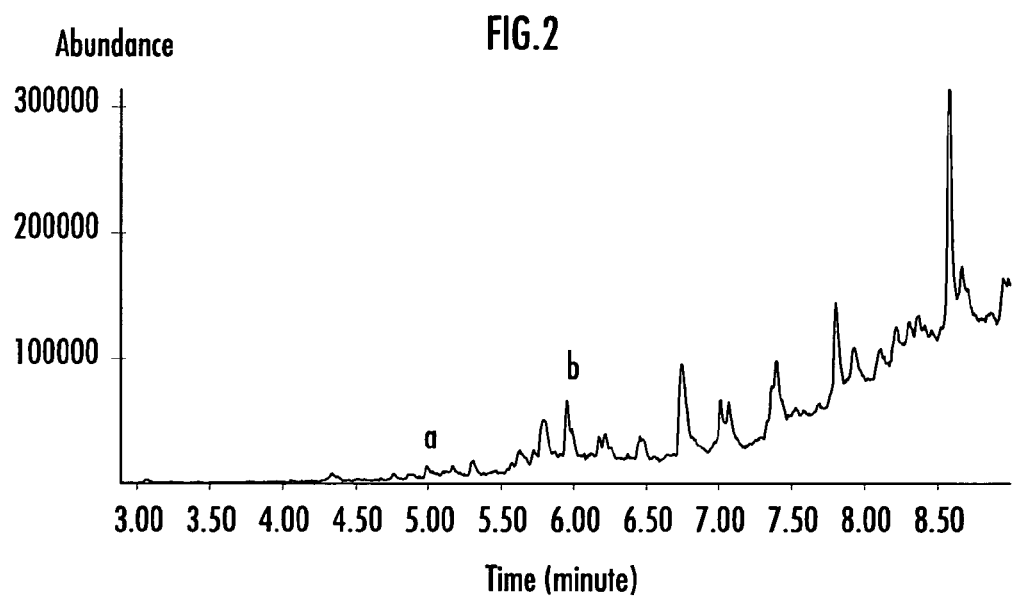
FIG. 2 is a gas chromatogram of a plurality of gas phase components produced when the analyzer of FIG. 1 is used for causing deterioration and decomposition of a polymer sample while exposing the sample to UV ray for 15 minutes under a humidified air atmosphere.
Figure 3:
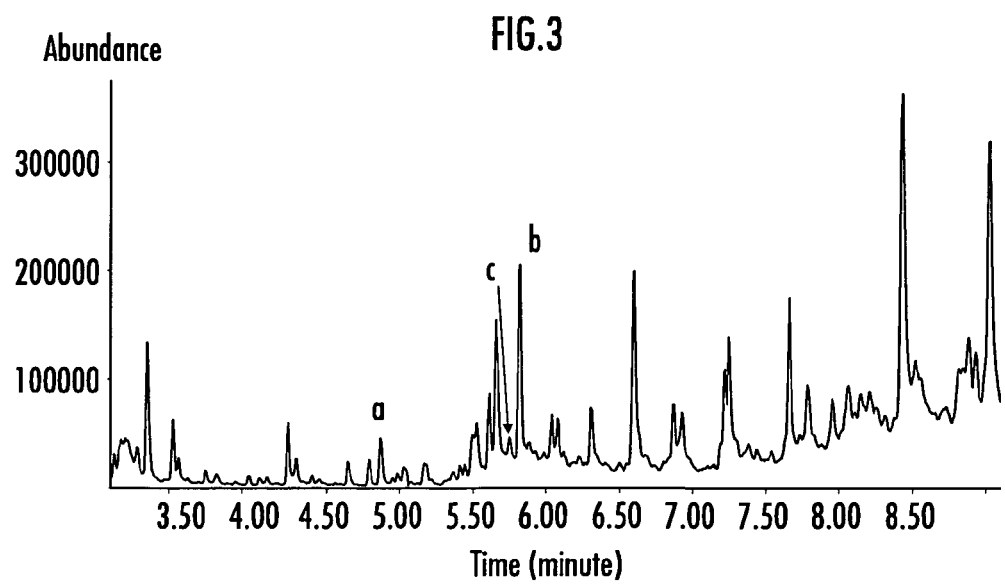
FIG. 3 is a gas chromatogram of a plurality of gas phase components produced when the analyzer of FIG. 1 is used for causing deterioration and decomposition of a polymer sample while exposing the sample to UV ray for 30 minutes under a humidified air atmosphere.
Figure 4:
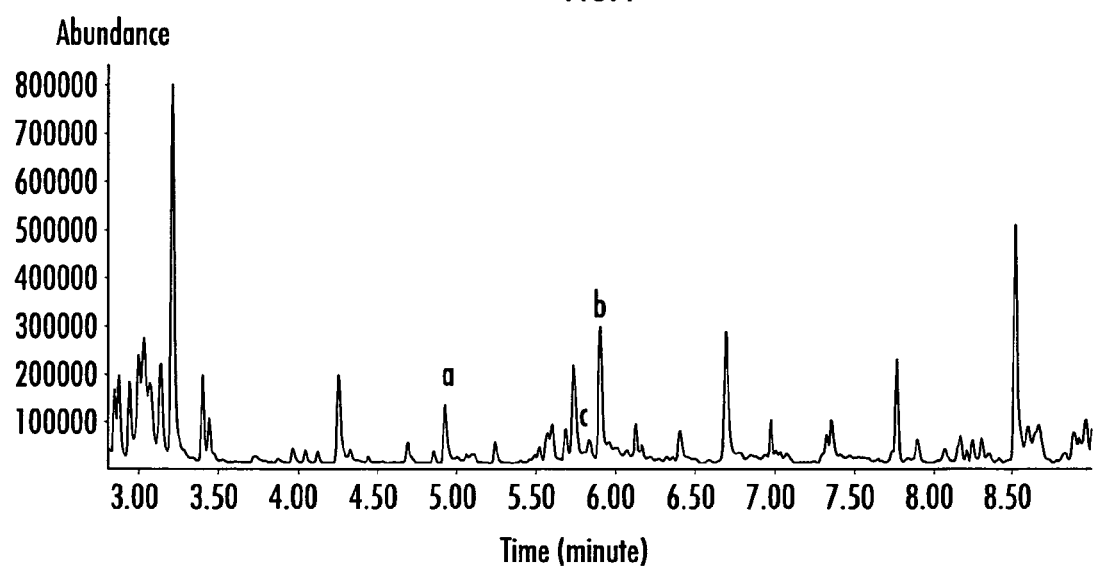
FIG. 4 is a gas chromatogram of a plurality of gas phase components produced when the analyzer of FIG. 1 is used for causing deterioration and decomposition of a polymer sample while exposing the sample to UV ray for 18 hours under a humidified air atmosphere.

It is apparent from FIGS. 2 to 4 that with an increase in the exposure time to UV ray, a larger number of components are produced and at the same time, they each shows a clearer peak. For example, the peaks a and b of FIG. 2 become clearer in FIG. 3 and the peak c which is not clear in FIG. 2 becomes clearer in FIGS. 3 and 4. The compounds corresponding to the respective peaks in these chromatograms can be identified by comparing the mass spectrum of each peak with the mass spectrum of a standard substance (for example, refer to Japanese Patent Laid-Open No. 2000-35422).

Figure 5:
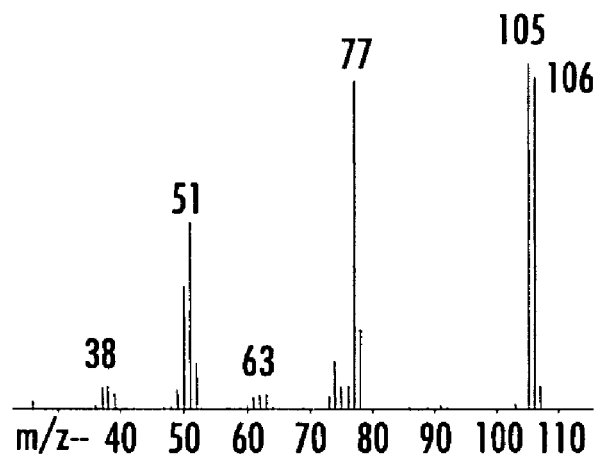
FIG. 5 illustrate the mass spectra of main peaks of the gas chromatogram shown in FIG. 4.
Figure 5B:
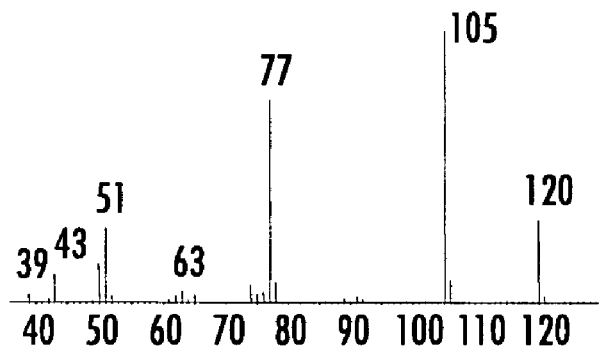
Figure 5C:
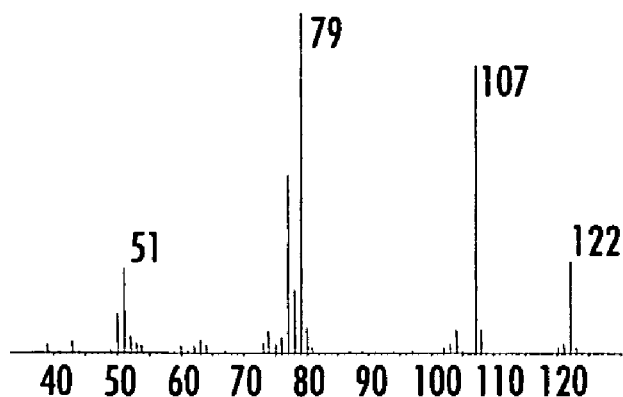

The mass spectrum of each of the peaks a, b and c in FIG. 4 are shown in FIG. 5(a), FIG. 5(b) and FIG. 5(c), respectively. The compounds of peak a, peak b and peak c are identified as benzaldehyde, phenylethanol and acetophenone respectively by comparing the mass spectra of FIG. 5(a), FIG. 5(b) and FIG. 5(c) with the mass spectrum of a standard substance.

Figure 6A:
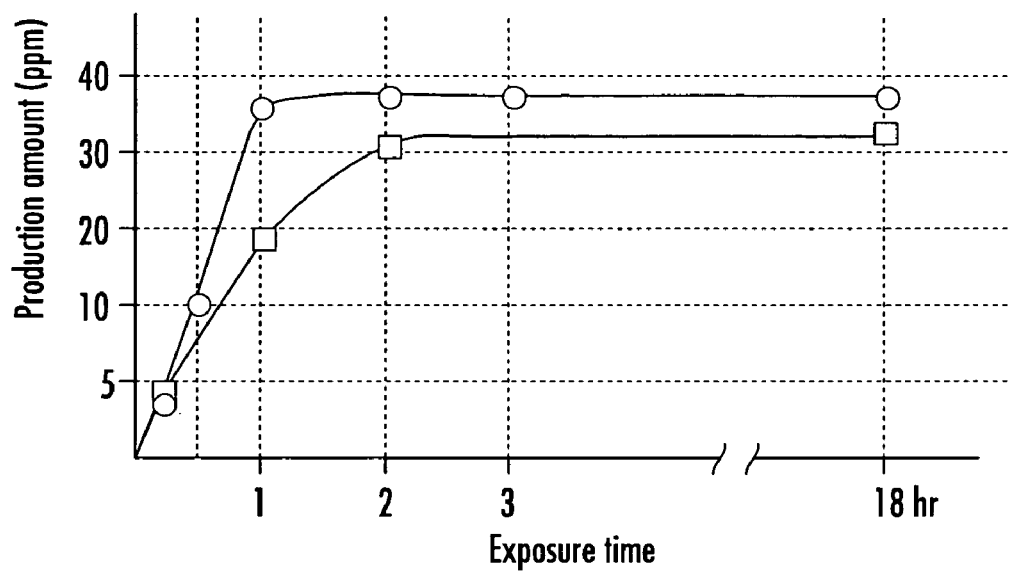
FIG. 6 is a graph showing a change in the production amount of gas phase components as a function of an exposure time to UV ray.
Figure 6B:
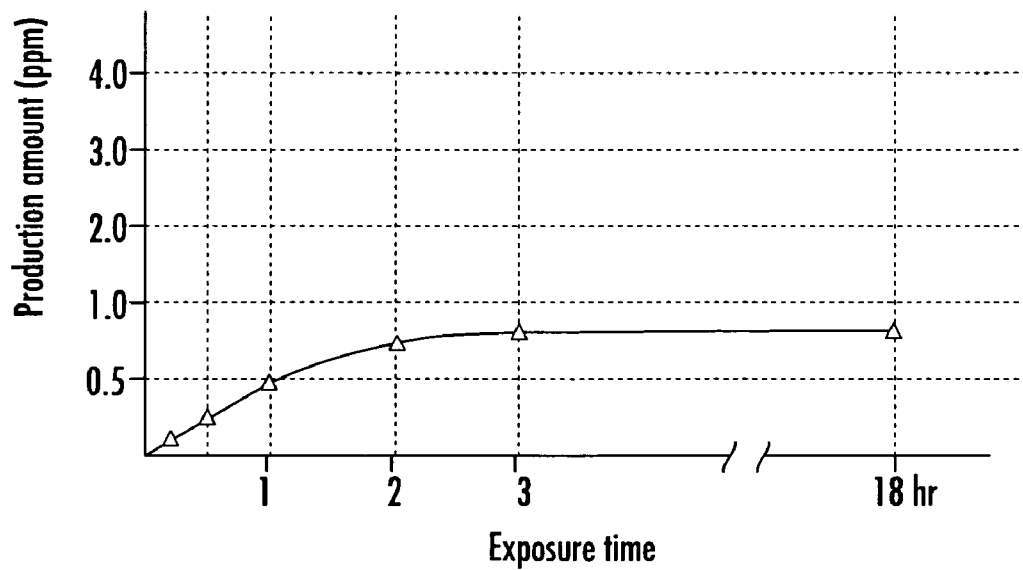

Changes in the production amounts of benzaldehyde, phenylethanol and acetophenone as a function of the exposure time to UV ray are shown in FIG. 6 as their concentration (ppm) with respect to all the gas phase components produced by the gas phase component production unit 2. It is apparent from FIG. 6(a) that the production amount of benzaldehyde reaches saturation within 1 hour after exposure to UV ray is started and that of acetophenone reaches saturation within 2 hours after exposure to UV ray is started. It is apparent from FIG. 6(b) that the production amount of phenylethanol reaches saturation within 3 hours after exposure to UV ray is started.

Accordingly, it has been elucidated that in the case of these benzaldehyde, phenylethanol and acetophenone, the deterioration test of polystyrene by light produced results within a period as short as about 3 hours.

These benzaldehyde, acetophenone and phenylethanol are presumed to be produced as a result of simultaneous reaction or secondary reaction between ozone generated by exposing the air to UV ray or water in the air with a styrene monomer, styrene dimer or the like which is a deterioration and decomposition product of polystyrene. The above-described reaction is illustrated below.

chemical findings on optical deterioration under a natural environment can therefore be obtained.

In this Embodiment, the gas introduction unit 3 is equipped with the carrier gas source 15 and gas switching device 17 so as to switch the gas to be introduced into the gas phase component production unit 2 from the atmospheric gas to the carrier gas after completion of the deterioration and decomposition of the polymer sample, thereby replacing the gas in the polymer sample analyzer 1 completely by the carrier gas. Alternatively, the gas switching device 17 may be disposed between the sample introduction portion 6 and the separation column 20 in order to replace only the gas in the separation column 20 by the carrier gas. In this case, the gas switching device 17 is composed of, for example, a three-way valve in order to introduce the carrier gas, which is fed from the carrier gas source 15 connected to the gas switching device 17, into the separation column 20 while preventing the atmospheric gas to be introduced into the gas phase component production unit 2 from being introduced into the separation column 20.

What is claimed is:

1. A polymer sample analyzer, comprising:
a gas phase component production unit having a housing and for producing a plurality of gas phase components in the housing;
a carrier gas introduction unit for introducing a carrier gas into the housing;
a separation unit for separating the gas phase components introduced therein from the housing via a sample introduction portion into each component; and
a detection unit for detecting the each component separated by the separation unit,

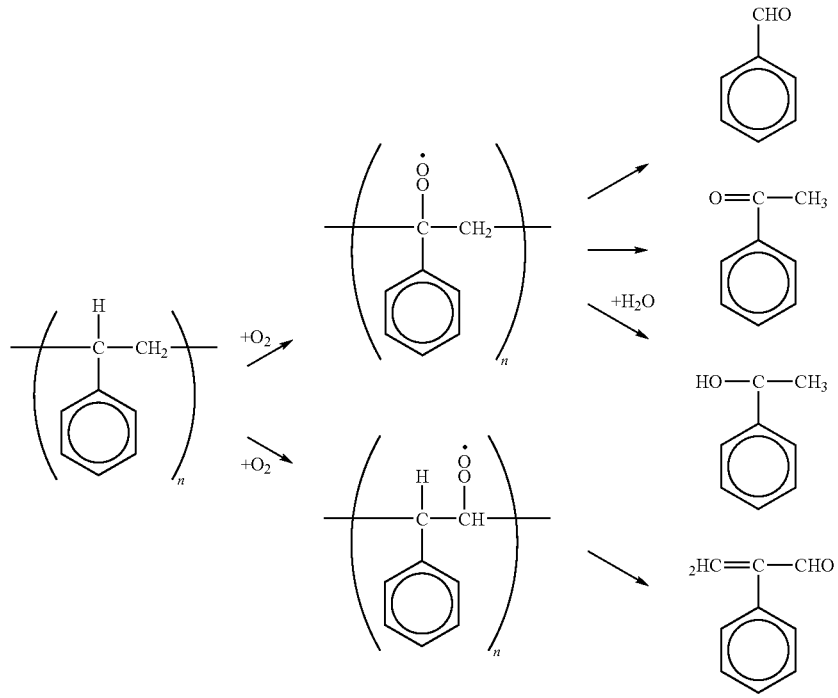

As described above, when a polymer sample is deteriorated and decomposed by exposing it to UV ray under the atmosphere of humidified air, a reaction similar to optical deterioration under a natural environment occurs. Many useful wherein the housing is directly connected to an upstream side of the sample introduction portion, a downstream side of the sample introduction portion is connected to an upstream side of the separation unit, and a downstream side of the separation unit is connected to an upstream side of the detection unit, and wherein the gas phase component production unit comprises, inside thereof, a silica tube having an upper end portion through which a sample vessel can be inserted and a lower end portion connected to the sample introduction portion, a UV irradiation unit for irradiating a polymer sample with UV rays, wherein the UV irradiation unit comprises (a) a lamp as a light source, (b) an optical filter for selectively transmitting ultraviolet light having wavelength of 400 nm or less from the light source, and (c) an optical fiber connected to the optical filter, wherein a tip portion of the optical fiber is inserted into the upper end portion of the silica tube in order to irradiate the polymer sample in the sample vessel, an atmospheric gas introduction unit for introducing a predetermined atmospheric gas into the gas phase component production unit, and a gas switching unit for switching a gas to be introduced into the separation unit between the carrier gas and the atmospheric gas; and wherein the polymer sample is, under the atmosphere of the predetermined atmospheric gas introduced from the atmospheric gas introduction unit, exposed to UV rays irradiated from the UV irradiation unit to cause deterioration and decomposition of the material, thereby forming a plurality of gas phase components and after the deterioration and decomposition of the polymer sample, the gas introduced into the separation unit via the housing and sample introduction unit is switched from the atmospheric gas to the carrier gas by the gas switching unit to introduce the gas phase components via the housing and sample introduction unit into the separation unit by the aid of the carrier gas.

2. A polymer sample analyzer according to claim 1, comprising a tube connected to the sample introduction portion and a flow rate control unit for controlling the flow rate of the gas phase components to be introduced into the separation unit by discharging a portion of the gas phase components from the sample introduction portion via the tube.

3. A polymer sample analyzer according to claim 1, comprising a gas phase concentrator for concentrating the gas phase components on a side of the sample introduction portion of the separation unit, and a gas phase component cooling unit for cooling the gas phase components at the gas phase component concentrator.

4. A polymer sample analyzer according to claim 1, wherein the gas phase component production unit is equipped with a heater disposed inside of the housing and configured to heat the polymer sample.

* * * * *